US010929916B2

(12) United States Patent
Abutair et al.

(10) Patent No.: US 10,929,916 B2
(45) Date of Patent: Feb. 23, 2021

(54) PERSONA BASED FOOD RECOMMENDATION SYSTEMS AND METHODS

(71) Applicant: MenuEgg LLC, Lawrenceville, GA (US)

(72) Inventors: Haytham Abutair, Lawrenceville, GA (US); Vijay Narayan, Alpharetta, GA (US)

(73) Assignee: MenuEgg, LLC, Lawrenceville, GA (US)

( * ) Notice: Subject to any disclaimer, the term of this patent is extended or adjusted under 35 U.S.C. 154(b) by 0 days.

(21) Appl. No.: 16/884,125

(22) Filed: May 27, 2020

(65) Prior Publication Data

US 2021/0004891 A1 Jan. 7, 2021

Related U.S. Application Data

(60) Provisional application No. 62/870,496, filed on Jul. 3, 2019.

(51) Int. Cl.
*G06F 17/00* (2019.01)
*G06Q 30/06* (2012.01)
(Continued)

(52) U.S. Cl.
CPC ......... *G06Q 30/0631* (2013.01); *G06F 9/547* (2013.01); *G06F 16/287* (2019.01); *G06F 16/9535* (2019.01); *G06F 16/9537* (2019.01); *G06N 5/04* (2013.01); *G06Q 30/0205* (2013.01); *G06Q 30/0282* (2013.01); *G06Q 30/0605* (2013.01); *G06Q 30/0623* (2013.01); *G16H 10/60* (2018.01); *G16H 20/60* (2018.01); *G16H 50/20* (2018.01)

(58) Field of Classification Search
CPC ............. G06F 19/9535; G06F 16/9535; G06F 16/9537; G06F 16/287; G06Q 30/0631; G06Q 30/0605; G06Q 30/0205; G06Q 30/0282
USPC ........ 715/745, 747, 818; 705/26.7, 15, 7.34, 705/14.53, 14.58, 14.66
See application file for complete search history.

(56) References Cited

U.S. PATENT DOCUMENTS 10,492,626 B2 * 12/2019 Auda .................... B41J 11/485
10,671,705 B2 * 6/2020 Capell ................ G06F 19/3481
(Continued)

OTHER PUBLICATIONS

Tarro, Restaurant-based intervention to facilitate healthy eating choices and the identification of allergenic foods at a family-oriented resort and playground, BMC Public Health, 17, 393 (Year: 2017).*

*Primary Examiner* — Stephen S Hong
*Assistant Examiner* — Matthew J Ludwig
(74) *Attorney, Agent, or Firm* — Hunt Pennington Kumar & Dula pllc

(57) ABSTRACT

The present disclosure relates systems and methods for food recommendations. More particularly, it teaches a systems and methods that can provide personalized menu item recommendations through a nutrient-focused machine learning model for nearby restaurants in near real-time, in order to assist in the selection of dishes that match a user's persona. Using these systems and methods enable a user to see a personalized prediction score of how much the system predicts that a particular user would like a particular dish.

7 Claims, 10 Drawing Sheets

FIG 8

(51) Int. Cl.
*G06F 16/9535* (2019.01)
*G06F 16/9537* (2019.01)
*G06F 16/28* (2019.01)
*G06F 9/54* (2006.01)
*G16H 20/60* (2018.01)
*G06N 5/04* (2006.01)
*G16H 10/60* (2018.01)
*G06Q 30/02* (2012.01)
*G16H 50/20* (2018.01)

(56) References Cited

U.S. PATENT DOCUMENTS

| | | | | |
|---|---|---|---|---|
| 10,692,396 B2* | 6/2020 | Bitran | | G16H 20/60 |
| 10,762,546 B1* | 9/2020 | Justin | | G06Q 50/12 |
| 2009/0164897 A1* | 6/2009 | Amer-Yahia | | G06F 3/00 |
| | | | | 715/703 |
| 2009/0204492 A1* | 8/2009 | Scifo | | G06Q 30/0603 |
| | | | | 705/14.36 |
| 2012/0191551 A1* | 7/2012 | Lutnick | | G06Q 20/20 |
| | | | | 705/15 |
| 2012/0239683 A1* | 9/2012 | Starkman | | G06F 16/9535 |
| | | | | 707/769 |
| 2013/0110582 A1* | 5/2013 | Starkman | | G06F 16/9535 |
| | | | | 705/7.29 |
| 2013/0159331 A1* | 6/2013 | Zhang | | G06F 16/29 |
| | | | | 707/758 |
| 2013/0166347 A1* | 6/2013 | Scotto | | G06Q 50/12 |
| | | | | 705/7.29 |
| 2013/0222406 A1* | 8/2013 | Wolfe | | H04L 67/02 |
| | | | | 345/582 |
| 2013/0325641 A1* | 12/2013 | Brown | | G06Q 30/0631 |
| | | | | 705/15 |
| 2014/0080102 A1* | 3/2014 | Krishna | | G09B 19/0092 |
| | | | | 434/127 |
| 2014/0236759 A1* | 8/2014 | Mirabile | | G06Q 30/0633 |
| | | | | 705/26.8 |
| 2015/0052098 A1* | 2/2015 | Kveton | | G06N 5/02 |
| | | | | 706/52 |
| 2015/0066915 A1* | 3/2015 | Golder | | G06F 16/9535 |
| | | | | 707/723 |
| 2017/0053362 A1* | 2/2017 | Galarraga | | G01N 33/0001 |
| 2018/0336592 A1* | 11/2018 | Kurra | | G06F 16/9535 |
| 2019/0122313 A1* | 4/2019 | Alemli | | G06Q 50/12 |
| 2019/0205942 A1* | 7/2019 | Gutnik | | G06Q 30/0631 |
| 2019/0205999 A1* | 7/2019 | Gutnik | | G06Q 50/12 |
| 2019/0370916 A1* | 12/2019 | Surkin | | G06Q 50/12 |
| 2020/0327976 A1* | 10/2020 | Pryor | | G06K 9/00671 |
| 2020/0380459 A1* | 12/2020 | Neumann | | G06Q 10/0832 |

* cited by examiner

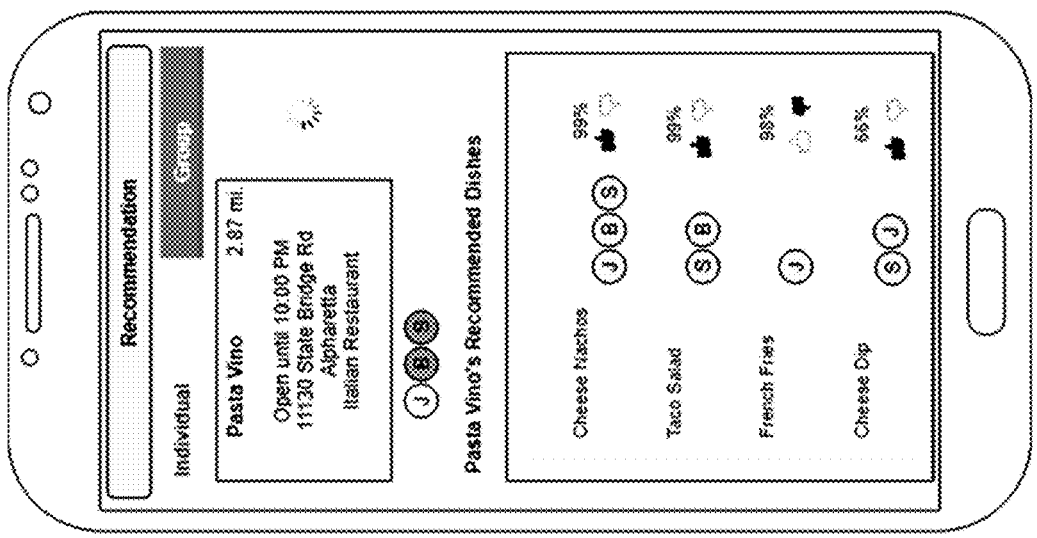
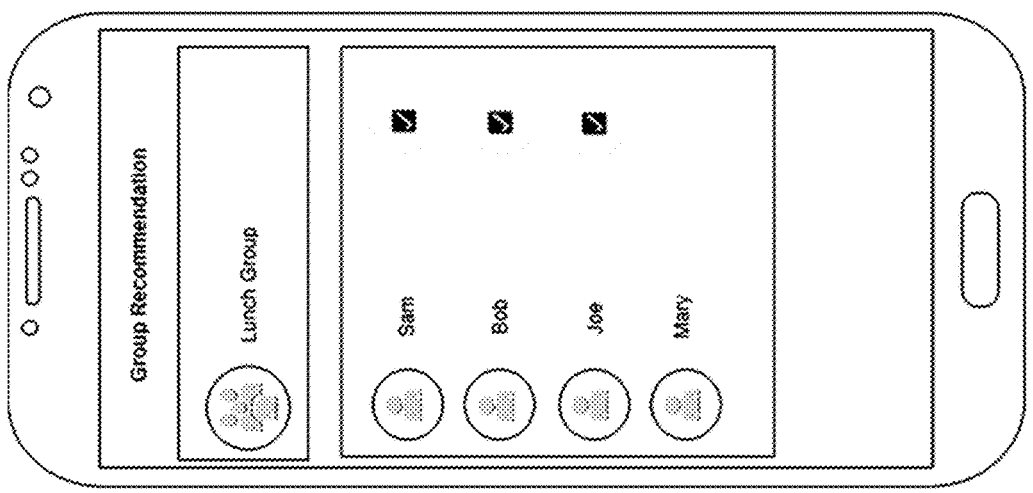
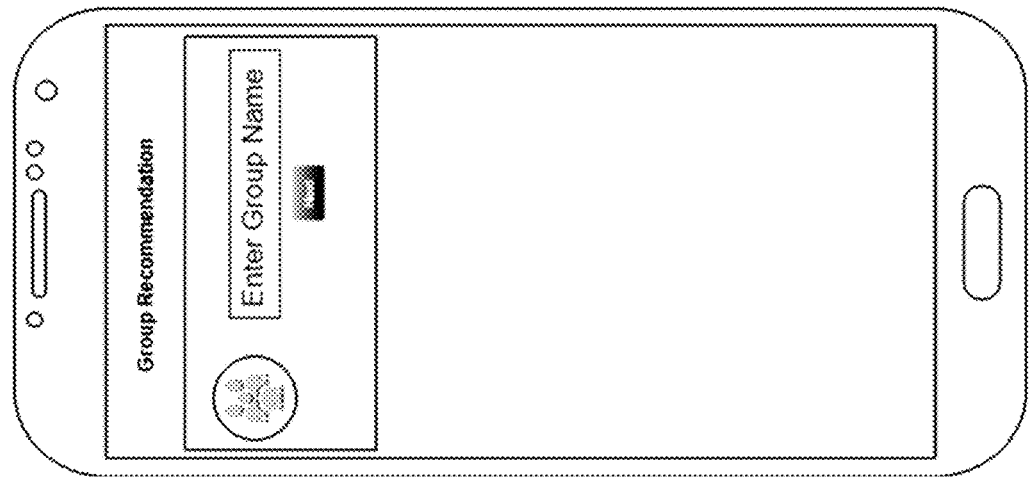
FIG 10

PERSONA BASED FOOD RECOMMENDATION SYSTEMS AND METHODS

CROSS-REFERENCE TO RELATED APPLICATIONS

This application claims benefit of the priority of U.S. Provisional Patent Application Ser. No. 62/870,496, entitled "Persona Based Food Recommendation Systems and Methods", filed Jul. 3, 2019. The entirety of which is hereby incorporated by reference.

FIELD OF THE INVENTION

This disclosure teaches a system and method for leveraging the nutrients within a dish to provide a user with personalized recommendations for restaurant menu items within a targeted geolocation that conform to the user's dietary preferences. The system can determine what category(s) that the dish potential falls under (carbs, protein, health-focused, etc. . . . ) and compare that with the personality of the user to find dishes that are potential matches to the user's persona and recommend those dishes to the user.

Registered users of system can select their persona and get the food recommendations provided to them via a suitable user interface, such as a smartphone mobile application. When the user selects a persona from the app, the system can search the restaurants nearby, collect the menu and their ingredients and run it through the system's custom Nutrient-Based Machine-Learning algorithm to get a personalized list of menus that match the user's persona. The user can provide feedback to the system in order to update and improve the system's model for that user.

BACKGROUND

Restaurant applications currently on the market fail to provide the following:
 Ability for users to proactively select what type of food they are in the mood for (in relation to dishes recommendations e.g. Food Delivery Services)
 Group recommendations for restaurants and dishes.
 Filtration of dishes based on dietary restrictions (allergies, high blood pressure, heart problems, etc.) and other desired dietary characteristics (low-carb, keto, etc.)
So, an issue with the present state of the art is that it lacks a system with the capability of can recommend restaurant dishes to a user based on that user's persona.

The above-mentioned shortcomings, disadvantages and problems are addressed herein, as will be understood by those skilled in the art upon reading and studying the following specification.

BRIEF DESCRIPTION OF THE INVENTION

This Summary is provided to introduce a selection of concepts in a simplified form that are further described below in more detail in the Detailed Description. This Summary is not intended to identify key or essential features of the claimed subject matter.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The present disclosure relates systems and methods for food recommendations. More particularly, it teaches a systems and methods that can provide personalized menu item recommendations through a nutrient-focused machine learning model for nearby restaurants in near real-time, in order to assist in the selection of dishes that match a user's persona. Using these systems and methods enable a user to see a personalized prediction score of how much the system predicts that a particular user would like a particular dish. By providing user feedback, such as by indicating that they liked or disliked the recommended dish, the system's machine learning component may adjust the user's personalized model accordingly in order to provide improved recommendations. The system facilitates this by applying the nutrients of the dish on which the user left feedback to the user's existing persona model to continuously learn and fine tune a user's taste. From there, the system adjusts the user's persona rating in order to provide better predictions over time.

In addition, users would have the ability to form groups with the people with whom they are with, or that are following them and have the system's machine learning algorithm apply to the group as a whole. The system uses a statistical approach in order to determine what restaurants to display first. Assuming the system has N users in a group, the system determines which categories have the highest intersection between each user and then displays each users dish recommendations.

An individual user or the admin of a group may select a central location about which the system may establish a restaurant search radius in order to set a geographic limitation on the recommendation results.

Users may see the dishes that were recommended for them as well as icons representing other user if those other users are also matched with the same particular dish. The recommendation percentage score for a particular user that is determined for each recommended dish may vary between users depending on their respective persona models and. For example, if two users matched for a specific dish, the system's machine learning algorithm could return a prediction score of 95% for user 1 and 89% prediction score for user 2. In embodiments a user's prediction score for a recommended dish may be provided to only that user.

To assist with dietary restrictions, the system can customize a baseline for a user's persona. For example, if a user has high blood pressure, nutritionist often recommend a low sodium diet, which may include only meals having less than 5 grams of sodium. In this example, this specific user's baseline for sodium may be much lower than that of an average user.

The customization of a user's baseline does not have to be limited to dietary restrictions due to medical conditions. It may also be applied to other dietary restrictions, such as food allergies, e.g. peanuts, or other discretional dietary limitations, e.g. a keto diet. By leveraging the USDA database, the system can generate idea as to what ingredients generally go into which dishes. This does not necessarily mean that a specific dish at a particular restaurant would have the exact ingredients that the system queried, but the system may use the common ingredients found in that type of dish to determine if a dish should be filtered out of the user's recommendation list.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

FIG. 10 is a drawing representing an exemplary workflow for group recommendations using the system.

DETAILED DESCRIPTION

Figure 1:
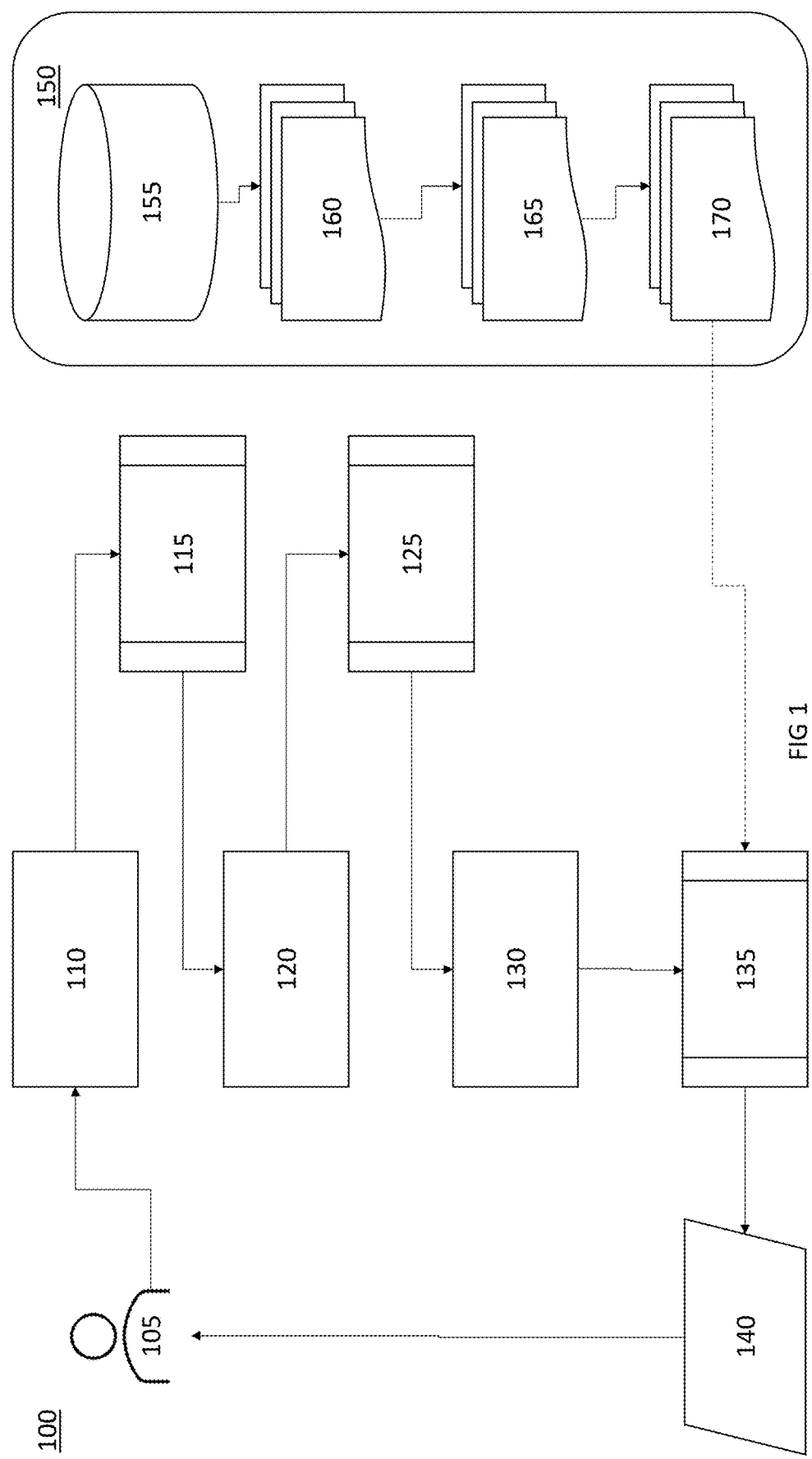
FIG. 1 is a drawing representing different stages of how the machine learning model may be generated from a raw food and nutrition database.

In the following detailed description, reference is made to the accompanying drawings which form a part hereof, and in which is shown by way of illustration specific embodiments which may be practiced. These embodiments are described in sufficient detail to enable those skilled in the art to practice the embodiments and disclosure. It is to be understood that other embodiments may be utilized, and that logical, mechanical, electrical, and other changes may be made without departing from the scope of the embodiments and disclosure. In view of the foregoing, the following detailed description is not to be taken as limiting the scope of the embodiments or disclosure.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprises" and/or "comprising" or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

It will be appreciated that for simplicity and clarity of illustration, where considered appropriate, reference numerals may be repeated among the figures to indicate corresponding or analogous elements. In addition, numerous specific details are set forth in order to provide a thorough understanding of the implementations described herein. However, it will be understood by those of ordinary skill in the art that the implementations described herein may be practiced without these specific details. In other instances, well-known methods, procedures and components have not been described in detail so as not to obscure the implementations described herein. Also, the description is not to be considered as limiting the scope of the implementations described herein.

The detailed description set forth herein in connection with the appended drawings is intended as a description of exemplary embodiments in which the presently disclosed apparatus and system can be practiced. The term "exemplary" used throughout this description means "serving as an example, instance, or illustration," and should not necessarily be construed as preferred or advantageous over other embodiments.

FIG. 1 shows an information flow for an exemplary method of using the system 100, and an expanded view of an embodiment of the Prediction Service. According to the embodiment depicted, a user 105 may provide user information 110, including dish category preference information and persona information, to the Provider Service 115. The Provider Service 115 may use the information provided to it to generate venue and menu information, which may be passed to the Nutrient Service 125. The Nutrient Service 125 may use the information that it receives from the Provider Service 115 to generate nutrient information, which the Nutrient Service 125 may pass to the Prediction Service 135. The Prediction Service 135 may use the information provided to it by the Nutrient Service 125 to generate recommendations, which may then be passed back to the user 105.

In an embodiment, a food nutrition mapper 160 may fetch details from a food/nutrition database 155, such as a USDA database, to create an input, which may then be sent to a persona mapper 165. The persona mapper 165 creates the mapping between the nutrients and the output classes. Finally, the data may be sent to and used by a machine learning algorithm within a model generator 170 for the purpose of learning and testing of the recommendation system 100 The learned model may then be saved and used by the Prediction Service 135 to run predictions against the input.

In an embodiment, the Prediction Service 135 may use the trained model provided by the model generator 170 to run predictions for the user based on the persona. The information from the food/nutrition database 155 may be passed to a food nutrition mapper 160. The food nutrition mapper 160 may associate menu items with nutritional content. The food nutrition mapper 160 may then pass information to a persona mapper 165, which may create the output classes required for the training of the model. The persona mapper 165 may then pass information to a model generator 170, which may use the input for training the machine learning algorithm. The model generator 170 may then save the trained model for the Prediction Service 135 to use for prediction against user's persona.

Figure 2:
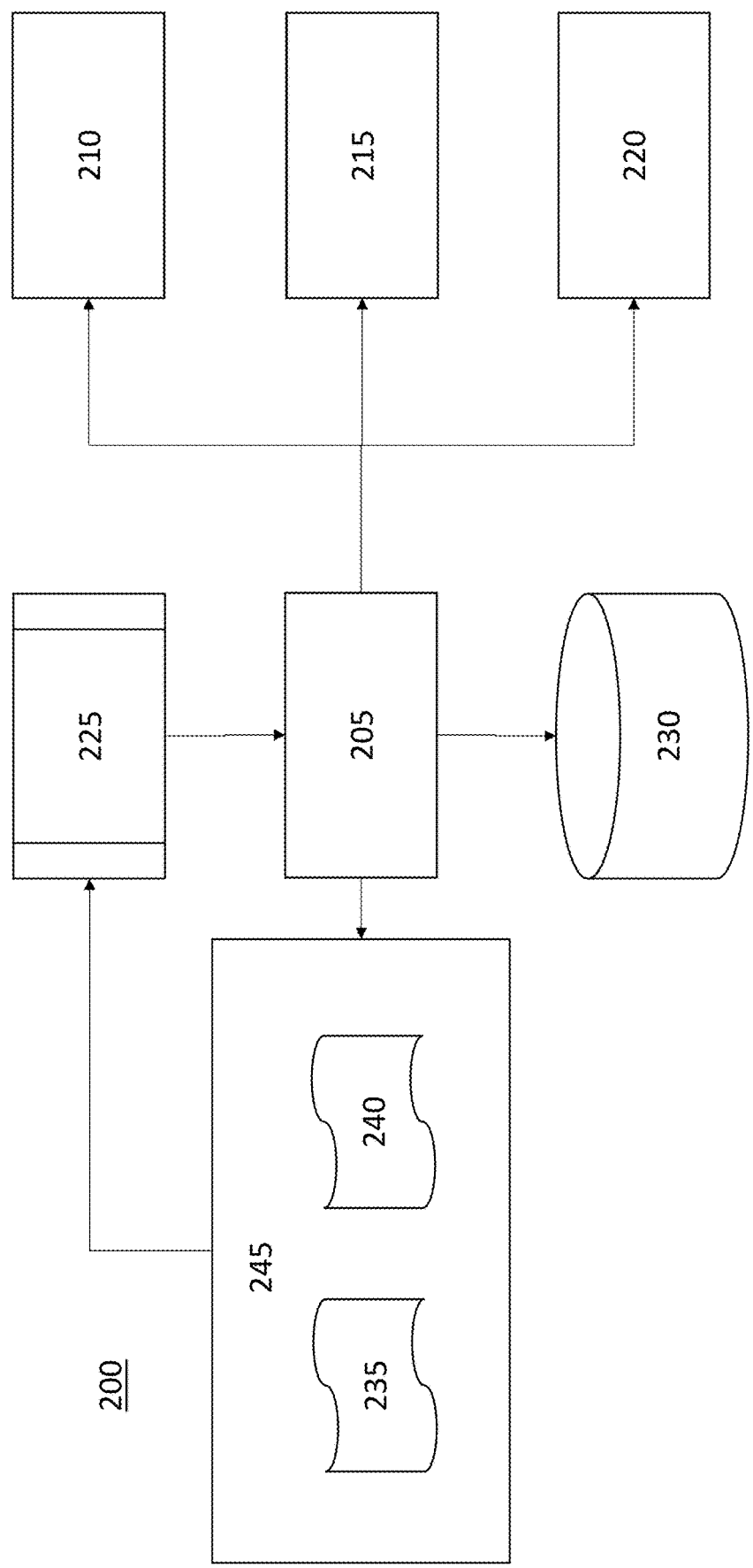
FIG. 2 shows an exemplary system diagram for a system for providing a user with personalized menu item recommendations.

FIG. 2 depicts a diagram of an exemplary system 200 in accordance with an embodiment. In the system 200 depicted the user interface 225 may pass information to the API Gateway 205 which may then receive information from information providers as well as a system database 230. This information may be passed to the Provider Service 210, the Nutrients service 215, and the Prediction Service 220 for analysis. Information from any of the Provider Service 210 the Nutrients service 215 and the Prediction Service 220 maybe passed to any of the other services or the database via the API Gateway 205. Information from these services may also be passed back to the user interface 225 via the API Gateway 205. Information from the services and user feedback provided via the user interface 225 may be passed to the database through the API Gateway 205 in order to update the model to better reflect user preferences. Communication between the user interface 225, the components of the system 200, and the API Gateway 205 may be through any suitable communications network, including but not limited to wired networks, wireless networks, 4 g networks, and the internet, generally.

In embodiments, the system's backend may consist of an API Gateway 205 orchestrating the calls to multiple microservices like the Provider Service 210, Nutrient Service 215 and Prediction Service 220. The API Gateway 205 may be the single interface for the mobile application. In other words, all calls to the backend of the system may be transmitted via the API Gateway 205. The API Gateway 205 may orchestrate the call through the system's internal services to recommend dishes to the user based on the user's persona and feedback.

The system's Provider Service 210 is responsible for performing restaurant and menu search functions within predetermined radii of the location provided by the user.

The system's Nutrient Service 215 is responsible for gathering the nutrient values for the menu items discovered by the Provider Service 210.

The system's Prediction Service 220 is responsible for running predictions against the trained model for the user and calculating the percentage match between menu items and the user's persona preferences. Dishes which have a prediction percentage above a predetermined threshold, such as 50%, 75%, etc., may be selected and returned to the user device as recommendations.

Figure 3:
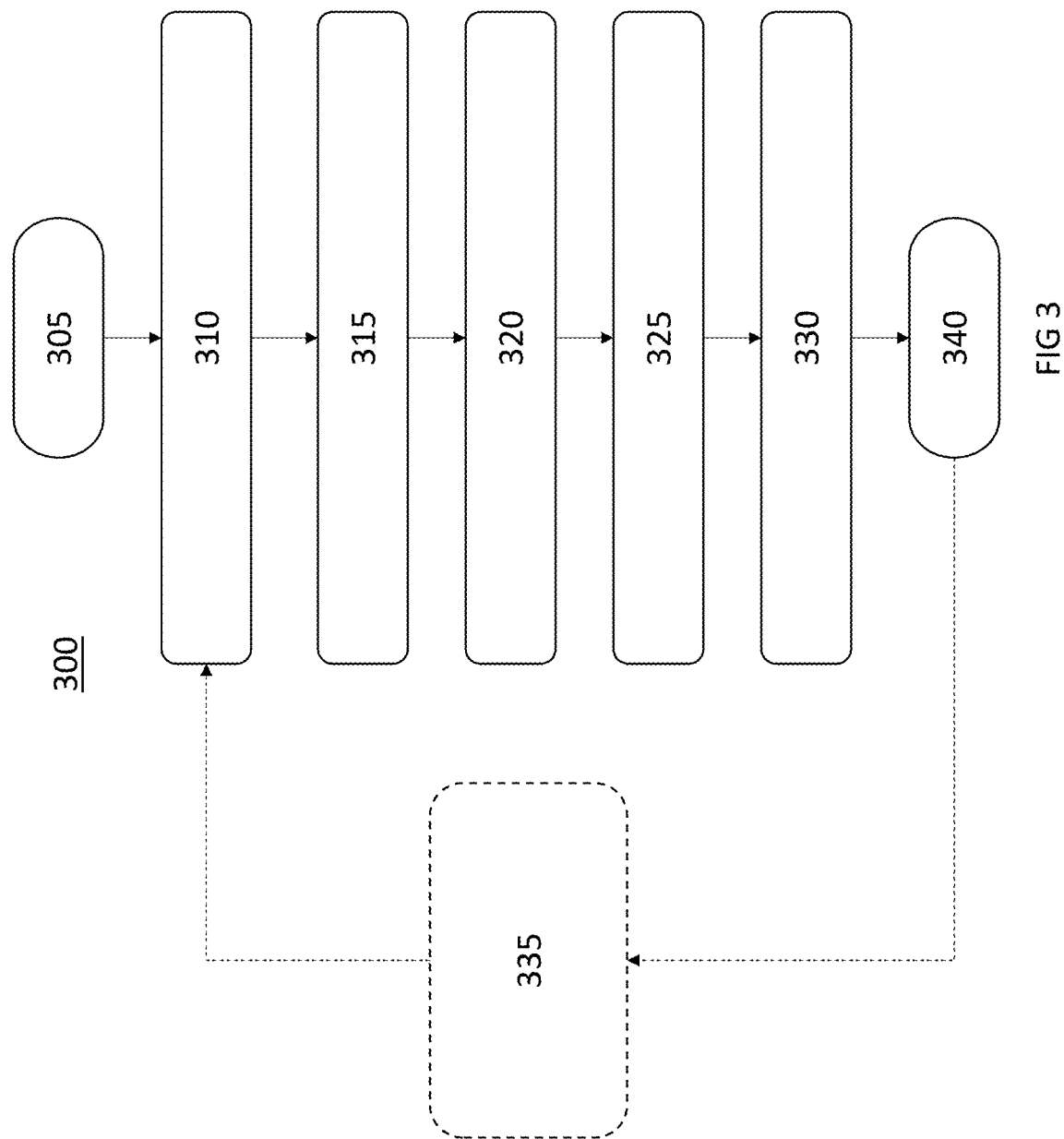
FIG. 3 depicts flowchart detailing an exemplary method of providing a user with personalized menu item recommendations based on a user's persona.

FIG. 3 depicts a flow chart showing an exemplary method 300 for providing a user with personalized menu item recommendations based on user persona and preferences. In the embodiment of the method 300 depicted in the flow chart of FIG. 3 a user may select 310 a persona and restaurant categories at the user device. This user information may then be used to search 315 restaurants that are within a given radius have a location provided by the user. The system may then procure 320 menu information from the restaurants identified in the search. The system may analyze 325 the menu information in order to determine 330 the nutrient information for menu items in the menus received. The system may do this through use of the Nutrient Service. The system made then take the information from the nutrients service and run it through the machine learning system that may be part of the Prediction Service. Once the system has analyzed 325 the menu items provided using the machine learning system it may provide 340 recommendations to the user. If the user desires, they may expand 335 the search parameters in which case the restaurant search radius about the location provided by the user may be increased and the steps following that action may be repeated. This process may be iterated n number of times with an expanding radius until the user selects a recommended dish or otherwise stops searching via the system.

Figure 4:
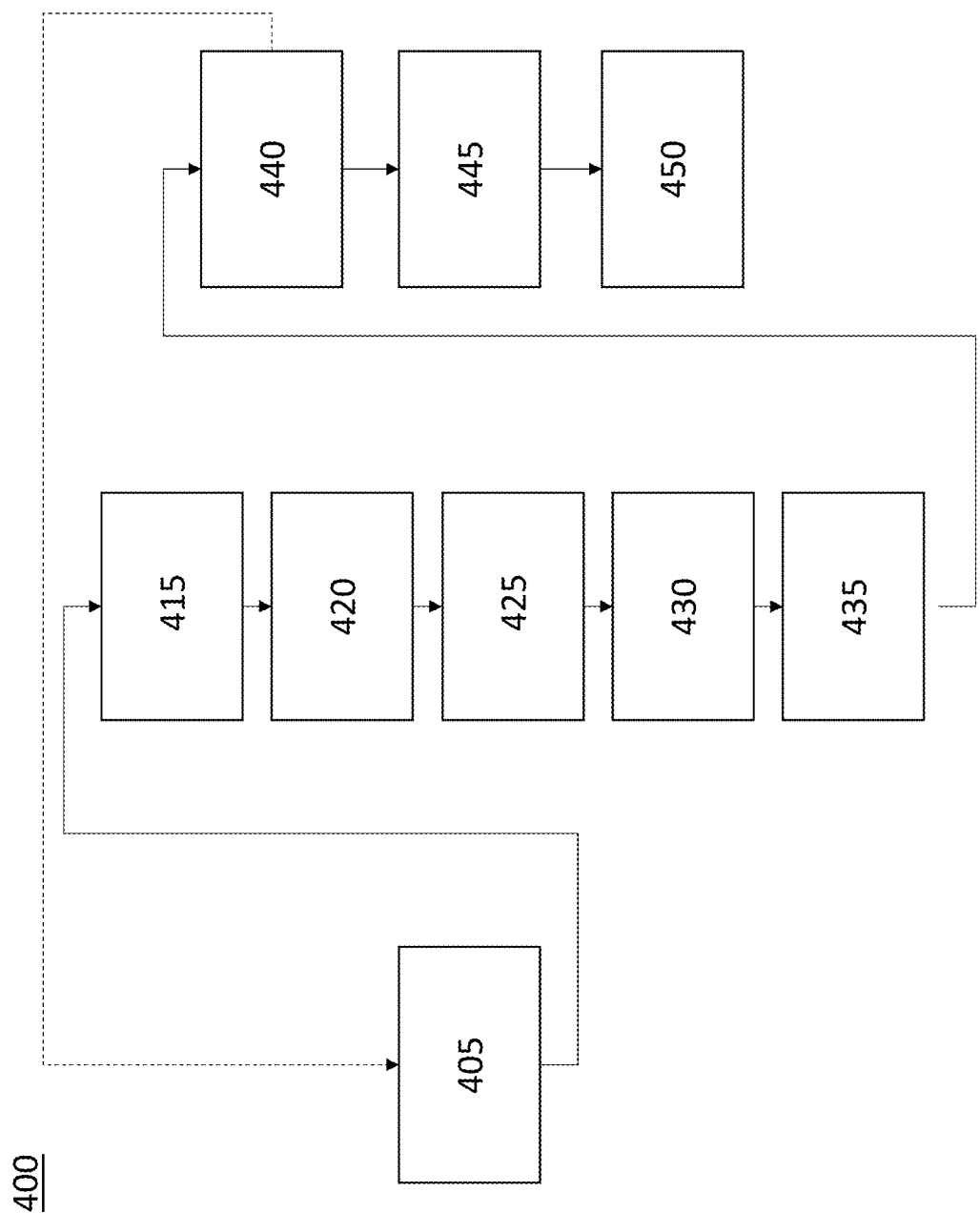
FIG. 4 is flowchart detailing an exemplary method of providing a user with personalized menu item recommendations based on user preferences defining a user persona.

An example of Pseudo Code for the system's predictive mechanism is shown below:

A. Get taste preference info, dietary preference info, and a location from the user profile
B. Set mile radius to x
C. Call Restaurant Provider Service to search restaurants and menu
D. Call Nutrient Service to collect nutrients for each menu
E. Call Prediction Service by passing the menu obtained in previous step
F. Discard menus that have a percentage match <50%
G. Return the response with restaurant details, menu, nutrients and persona percentage
H. Go to step B with a greater x value
I. Keep repeating the above steps for greater miles FIG. 4 depicts and embodiment of a method 400 for providing a user with personalized menu item recommendations based on user preferences. In this embodiment the following steps may occur:

User inputs 405 a persona and the taste categories like Thai, American, etc., for which they want to see the recommended food choices The system searches 415 for nearby restaurants and menu information.

Menu information is collected and sent 420 to the Nutrient Service to determine their nutrients.

The system identifies 425 the nutritional characteristics of menu items.

The menu and their nutrients are then sent to the Prediction Service where the nutrients are compared 430 against the trained machine learning mode to determine a percentage match.

Menu items that fail to meet preset requirements based on persona and input information are discarded 435.

The system then returns 440 menu items with match percentages greater than or equal to the predetermined threshold to the user via the user interface Steps 405-440 may be with an increased search radius if the user wants to view recommended menu items from more restaurants.

A user may provide 445 the system with feedback, such as indicating that they liked or disliked a menu or menu item.

The system allows multiple ways to update 450 the model to improve prediction for the user persona. The machine learning model may update the model for the user based on user feedback to provide improved recommendations for that user in the future. The model may also be updated when a user tags a menu or photo.

Figure 5:
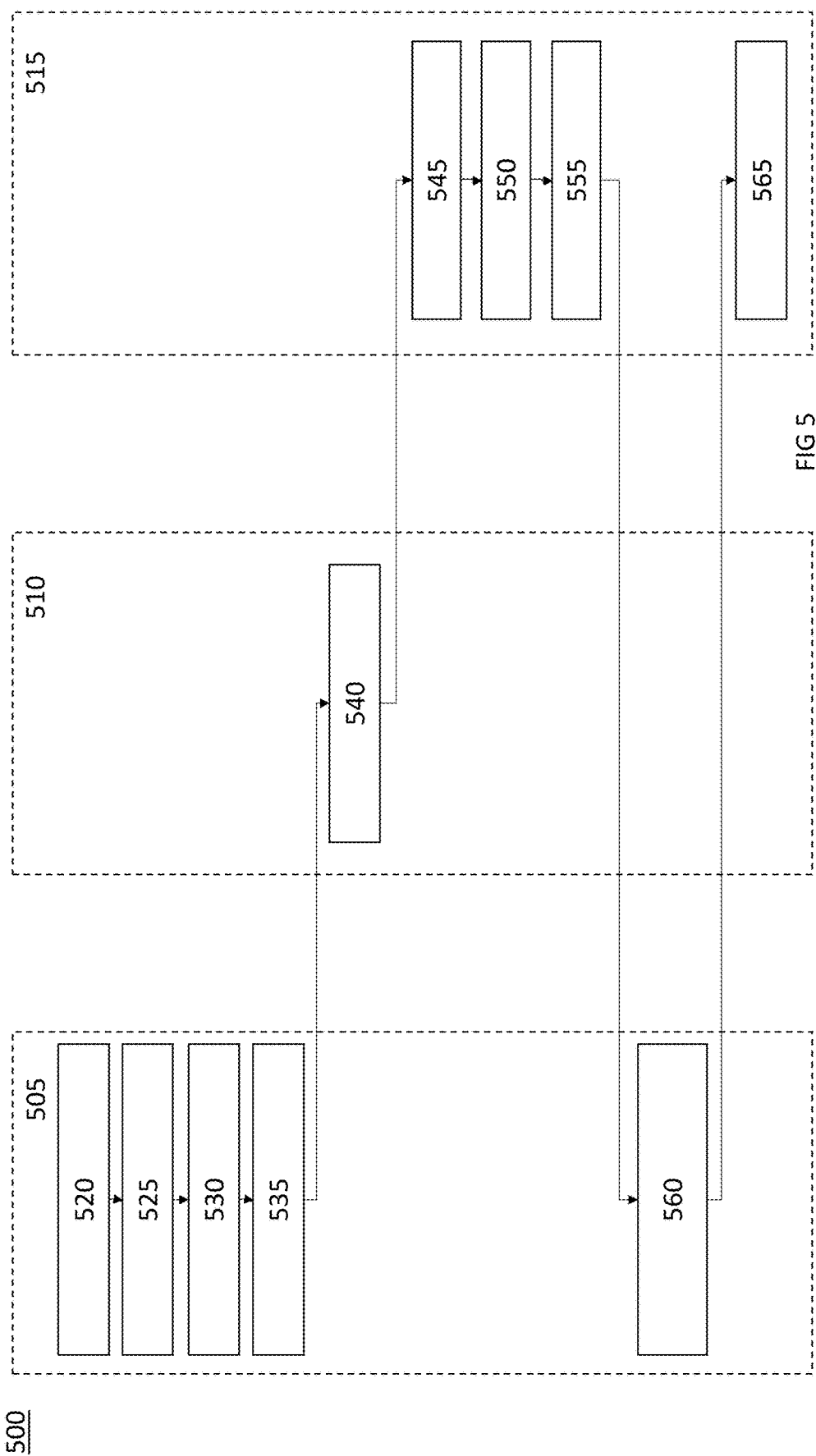
FIG. 5 depicts a flowchart detailing an exemplary information flow for providing a user with personalized menu item recommendations based on a user persona across components of the system for the same.

FIG. 5 shows an embodiment of a manner in which information may flow across different service elements of the system. The Provider Service 505 receives 520 user information from a user's account. This user information may include a location, a radius distance, food preference information, and dietary preference information. The Provider Service 505 may then set 525 the user provided location as the center of the search area for the restaurant search 530. The Provider Service 505 may then search 530 an area within the provided radius distance of the user provided location. Once the Provider Service 505 has identified restaurants within the search area it may then collect 535 menus from each of the identified restaurants. Once the Provider Service 505 collects the menus from these restaurants the system may then pass the menu information from the Provider Service 505 to the Nutrient Service 510. Once received, the Nutrient Service 510 may analyze 540 the menus provided by the Provider Service 505 in order to determine the characteristics of the dishes present in said menus. The Nutrient Service 510 may place the different menu items into categories based on the macro nutrients present therein, or by other quantifiable characteristics. Once the Nutrient Service 510 analyzes the dishes provided in the menus it may then pass the analyzed dish information to the Prediction Service 515. The Prediction Service 515 may then compare 545 the dish information against the user provided food preference information and dietary preference information in order to determine what dishes are likely to correspond to the desires of the user. The Prediction Service 515 may cull the less likely to be desirable dishes by rejecting any dish that is in a particular category which does not match the user preferences, or by rejecting 550 any dish that falls more than a predetermined amount of variance from said preferences. Once the Prediction Service 515 culls the dishes that correspond the least to the user preferences it may then return 555 the higher probability matches to the user. If the user then selects one of the dishes returned by the Prediction Service 515, they may provide 560 feedback to the system. If the user provides feedback on a dish that was recommended by the system that feedback may be sent to the Prediction Service 515 which may use said feedback to update 565 the prediction model for that user.

Figure 6:
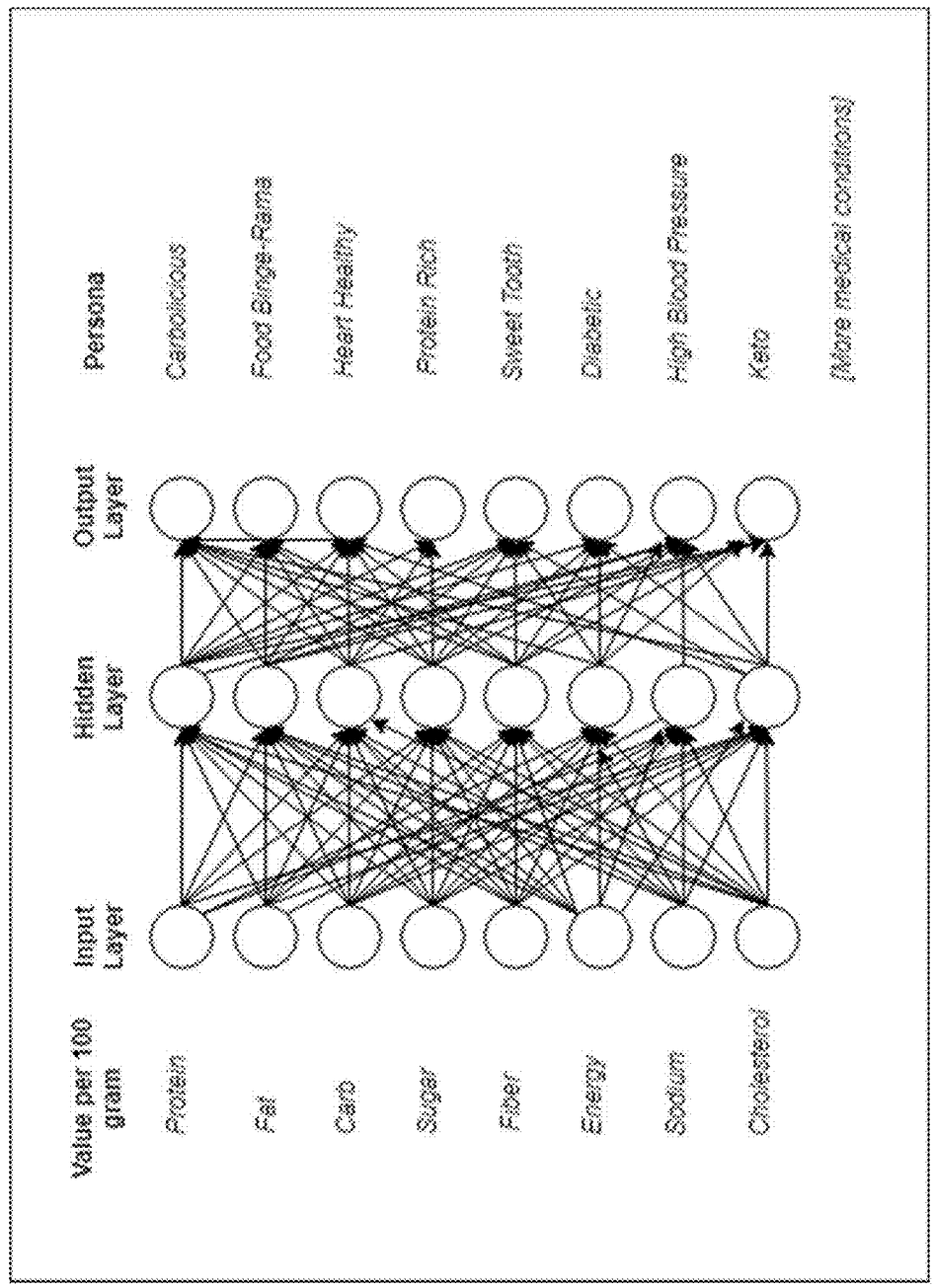
FIG. 6 depicts an exemplary 3-layer neural network that the system may use to train the model.

FIG. 6 depicts an embodiment of the machine learning model that the system may use to analyze the menu items and provide the user with recommendations of dishes that correspond to their preferences. The system's machine learning model is a multi-class, multi-label classifier neural network that is trained to predict the persona(s) from databases of dishes and their nutrients. The different classes are directly mapped to the persona that the user would choose. Categories into which the dishes may be categorized may vary according to the users desires and the system parameters. In the embodiment depicted in FIG. 9 these categories are "Carbolicious, Food Binge-Rama, Heart Healthy, Protein, Sugary, Diabetic, Blood Pressure and Keto". Inputs into the neural network may be provided in the 100-gram equivalent value of the nutrients for each dish analyzed. The following nutrient values are selected for training and prediction "Protein, Carb, Fat, Sugar, Fiber, Energy, Sodium, and Cholesterol".

Pseudo Code for creating example output classes for model training:

```
If Protein > 20 Then
    Class = "Protein Rich"
If Fat > 20 Then
    Class = "Food Binge-Rama"
If Sugar >= 22.5 Then
    Class = "Sweet Tooth"
If Fat < 20 And Sodium < 700 And Cholesterol < 67 Then
    Class = "Heart Healthy"
If Sugar < 22.5 And Fat < 20 And Carb < 60 Then
    Class = "Carbolicious"
If Sugar < 20 And Carb < 50 Then
    Class = "Diabetic"
If Sodium < 500 Then
    Class = "Blood Pressure"
If Carb < 30 And Fat >= 50 Then
    Class = "Keto"
```

Figure 7:
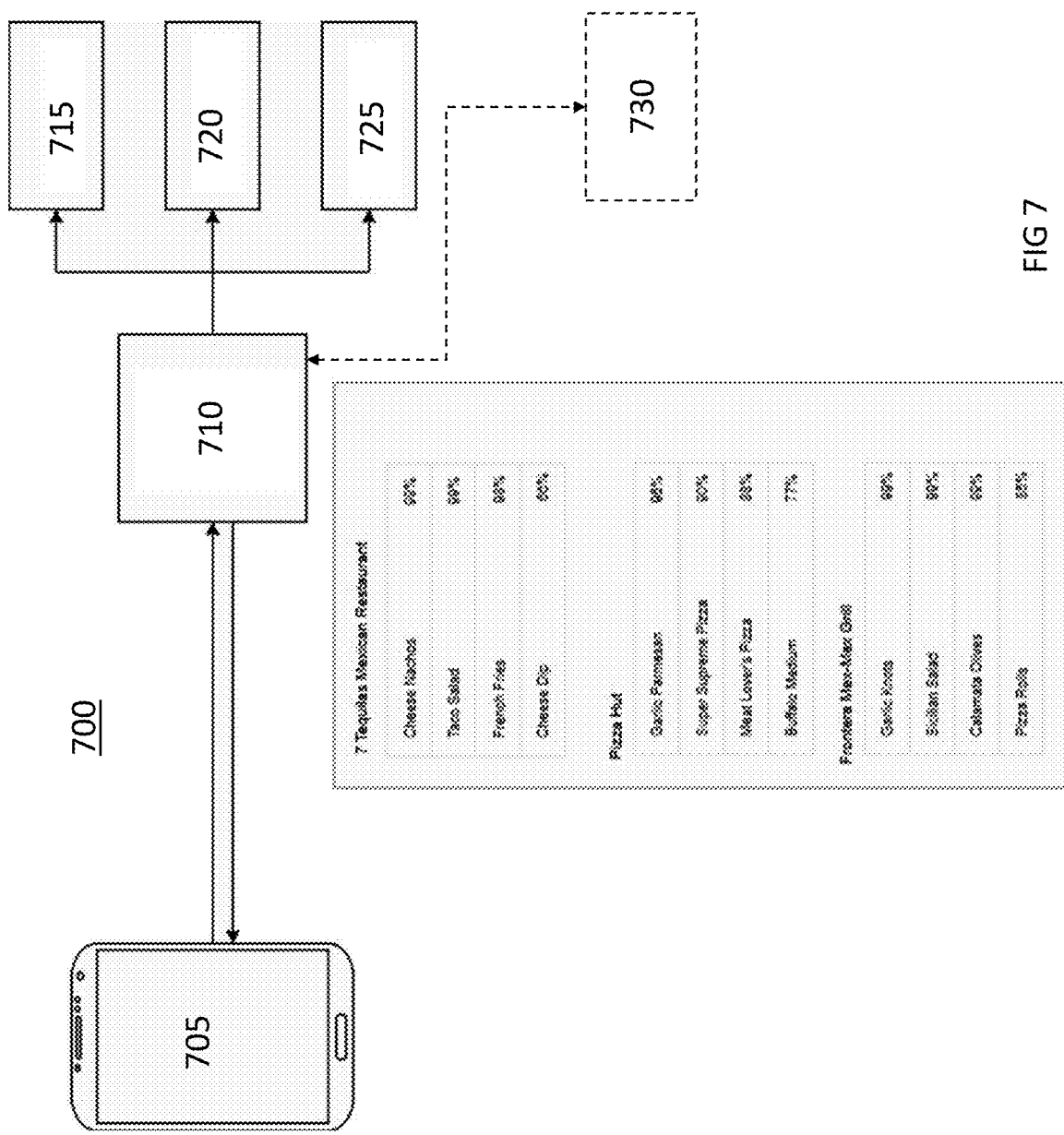
FIG. 7 is a drawing of a networked environment including the gateway, restaurant Provider Service, nutrients service, and the Prediction Service.

FIG. 7 depicts a simplified system diagram wherein a user device 705 may communicate information to the system through an API Gateway 710. Components of the system may include a Provider Service 715, a Nutrient Service 720, and a Prediction Service 725. In embodiments, the Nutrient Service 720 may communicate with third party service providers 730 to provide information or otherwise assist with analysis of menu items provided to the system. In embodiments, the Provider Service 715, Nutrient Service 720, and the Prediction Service 725 may communicate between each other directly instead of passing first through the API Gateway 710.

Figure 8:
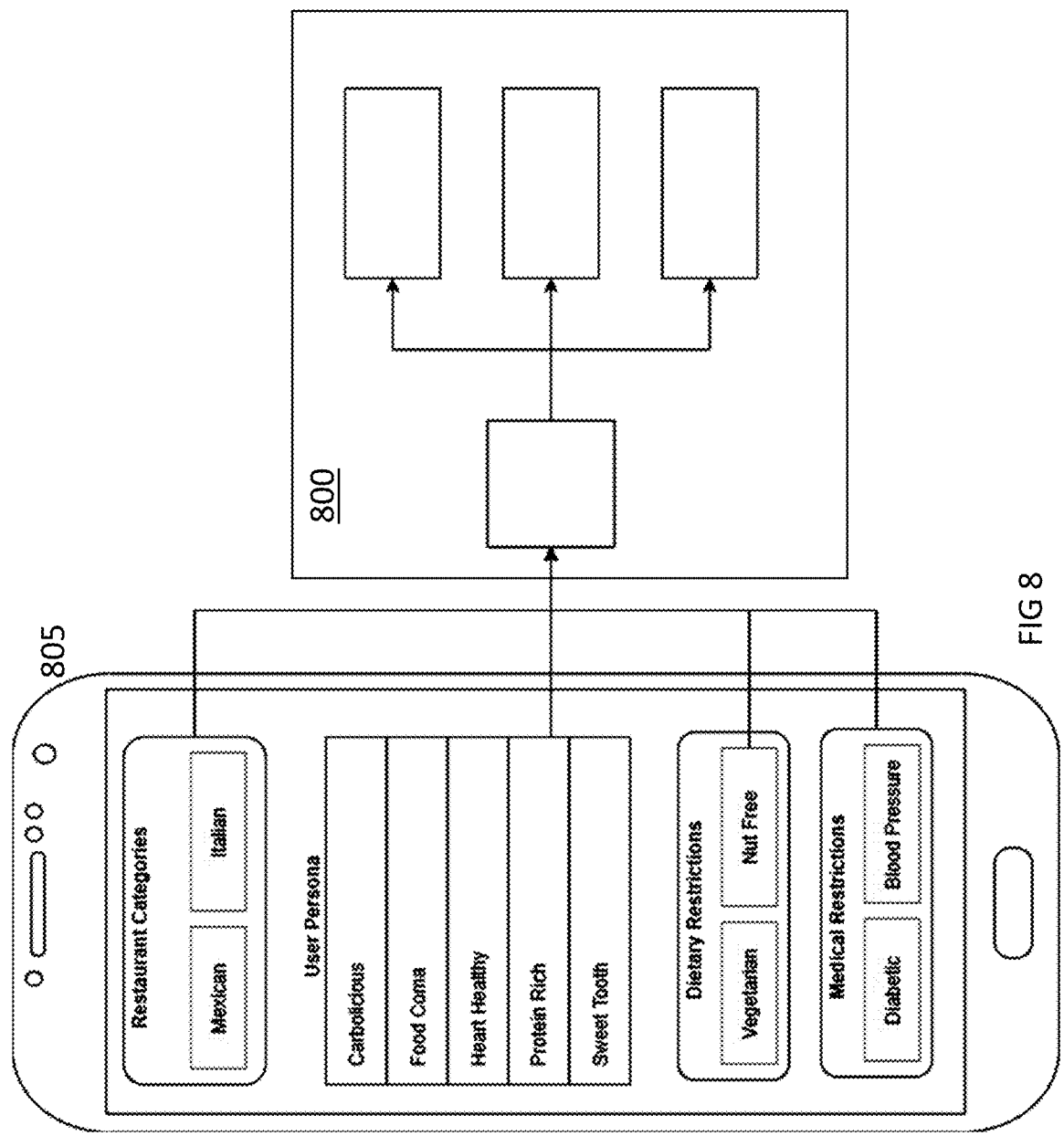
FIG. 8 is a drawing of an exemplary system rendered in a network environment where the restaurant categories and the persona are selected by the user and sent to the gateway service.

FIG. 8 depicts an exemplary embodiment of a user interface 805 with which a user may provide user preference information to the system 800.

Figure 9:
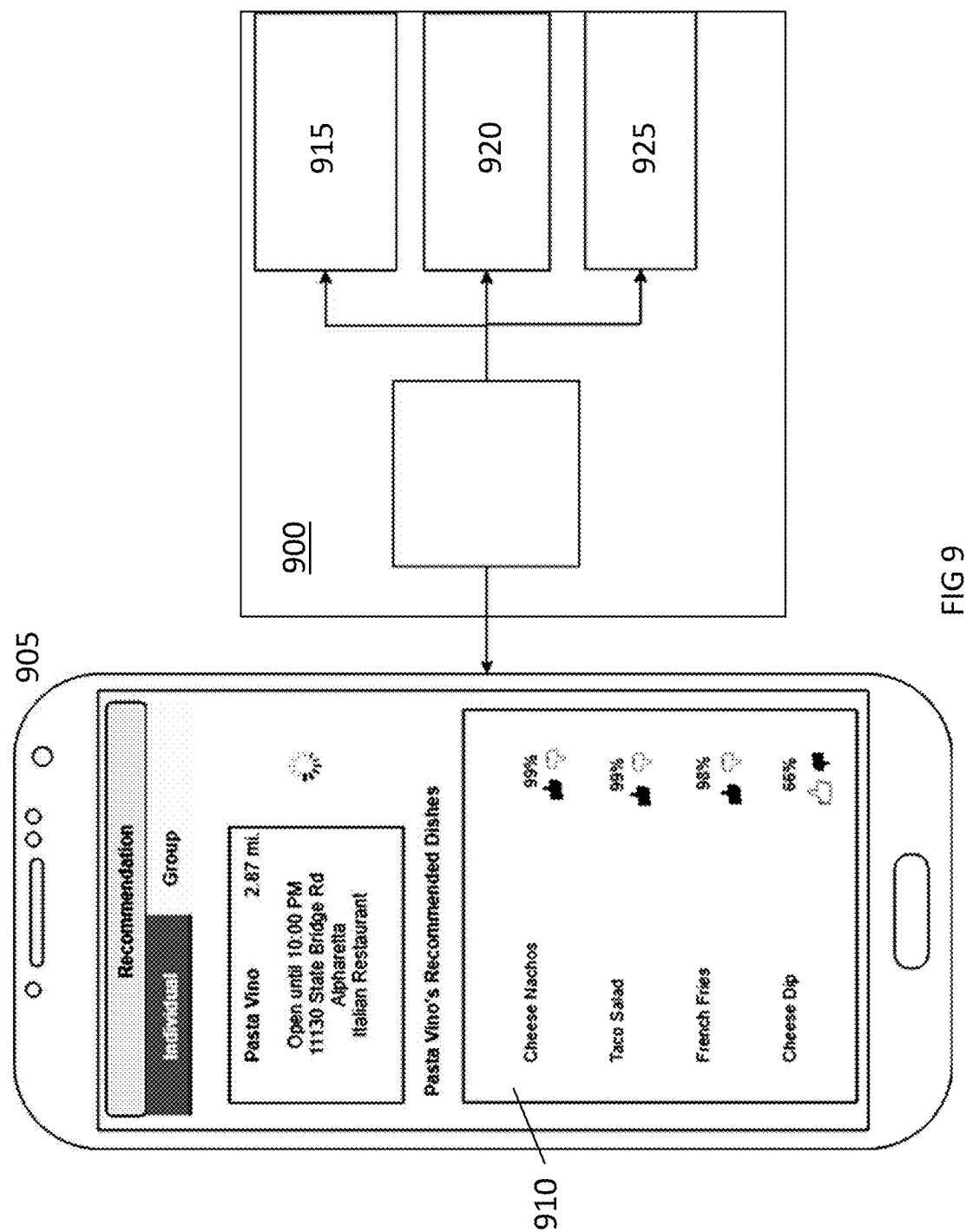
FIG. 9 is a drawing of another example user interface of the system rendered in the network environment where the personalized menu is displayed to the user along with the matching percentages.

FIG. 9 depicts an exemplary system 900 like that shown in FIGS. 1 and 2, further including an exemplary embodiment of a user interface 905 showing recommendations provided to the user device by the Prediction Service 925 portion of the system 900. The user interface 905 may be used to provide feedback to the system 900, here shown in the form of thumbs up and thumbs down buttons, which may be used by the system 900 to update the user model and otherwise update the system parameters in order to better serve the persona of the specific user.

FIG. 10 shows examples of possible user interface screens on a user device with which a user may interact with the system. The user interface screens shown in the figure depict a possible way the system may be used to provide menu item suggestions for a group of people. The group menu item suggestion method implemented by the system may identify which menu items have high correlation to the different personas of the group members.

In the example depicted, all of the users' preferred categories are categorized via determining the intersection of the categories selected by the various users in the group. Any categories that are left out are then added as part of a union. For instance, if User1 selects Italian, Mexican and American as categories and User2 selects Italian, Indian and Mexican, then the intersection of categories, i.e. Italian and Mexican will be considered as the primary categories for our search.

In the example depicted in the figure, "Pasta Vino" is a restaurant (Italian) where both Bob and Sam prefer to eat, but which Joe does not prefer. Within this restaurant, the system's Machine Learning algorithm is applied using each users' personas resulting in the system returning recommended dishes with the associated percentage for each unique user. In the example, Taco Salad was suggested for both Sam and Bob but not for Joe. This is because the Taco Salad dish's nutrient facts, based on USDA data, falls under the healthy persona. Given that Sam and Bob have Healthy selected as their persona while Joe has another persona selected, this dish would not be recommended for Joe, and hence why his icon does not appear next to the icon for that dish.

Apparatus, methods and systems according to embodiments of the disclosure are described. Although specific embodiments are illustrated and described herein, it will be appreciated by those of ordinary skill in the art that any arrangement which is calculated to achieve the same purposes can be substituted for the specific embodiments shown. This application is intended to cover any adaptations or variations of the embodiments and disclosure. For example, although described in terminology and terms common to the field of art, exemplary embodiments, systems, methods and apparatus described herein, one of ordinary skill in the art will appreciate that implementations can be made for other fields of art, systems, apparatus or methods that provide the required functions. The invention should therefore not be limited by the above described embodiment, method, and examples, but by all embodiments and methods within the scope and spirit of the invention.

In particular, one of ordinary skill in the art will readily appreciate that the names of the methods and apparatus are not intended to limit embodiments or the disclosure. Furthermore, additional methods, steps, and apparatus can be added to the components, functions can be rearranged among the components, and new components to correspond to future enhancements and physical devices used in embodiments can be introduced without departing from the scope of embodiments and the disclosure. One of skill in the art will readily recognize that embodiments are applicable to future systems, future apparatus, future methods, and different materials.

All methods described herein can be performed in a suitable order unless otherwise indicated herein or otherwise clearly contradicted by context. The use of any and all examples, or exemplary language (e.g., "such as"), is intended merely to better illustrate the disclosure and does not pose a limitation on the scope of the disclosure unless otherwise claimed. No language in the specification should be construed as indicating any non-claimed element as essential to the practice of the disclosure as used herein.

Terminology used in the present disclosure is intended to include all environments and alternate technologies that provide the same functionality described herein.

The invention claimed is:

1. A method for providing personalized menu item recommendations via a persona-based food recommendation system, comprising the steps of:
   receiving user information comprising:
      a location;
      a distance radius;
      menu item feedback;
      taste preference information;
      dietary preference information;
   creating a user persona model based on the received user information via a machine learning system, wherein the model is based at least upon a mapping between nutritional content of the feedback menu item and the model wherein the nutritional content is classified in an output class;
   identify restaurants being within the distance radius from the location
   collecting menus from the identified restaurants
   identify menu items from the collected menus
   determining nutritional content of the identified menu items, said determining performed by comparison of the identified menu items against known nutritional information from similar items stored in a database;
   selecting identified menu items determined to have nutritional content corresponding to the user persona model, said selecting comprising calculating a percentage match between the selected menu items and the user persona model and returning at least one of the selected menus item having a percentage match above a predetermined threshold; and
   transmitting the at least one selected menu item to a user interface.

2. The method of claim 1, further comprising the step of:
   in response to determining nutritional content of the identified menu items, classifying the identified menu items into at least one category.

3. The method of claim 1, wherein the user information additionally comprises at least one of:
   medical information; and
   biometric information.

4. The method of claim 1, further comprising the steps of:
   requesting updated user information;
   receiving the updated user information; and
   identifying restaurants based on the updated user information.

5. The method of claim 1, further comprising the step of:
   receiving user input responsive to the transmission of the at least one selected dish; and
   updating the user information based on the user input.

6. The method of claim 2, wherein the at least one category comprising:
   carbohydrate rich;
   fat rich;
   heart healthy;
   protein rich;
   sugar rich;
   diabetic;
   high blood pressure; and
   ketogenic.

7. The method of claim 1, further comprising the step of:
   receiving user feedback; and
   updating the user persona model responsive to said user feedback.

* * * * *